US00PP37500P2

(12) United States Plant Patent
Mathey

(10) Patent No.: US PP37,500 P2
(45) Date of Patent: Jun. 30, 2026

(54) ***ACER PALMATUM* PLANT NAMED 'SMNAPK'**

(50) Latin Name: *Acer palmatum*
Varietal Denomination: SMNAPK

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,892

(22) Filed: Oct. 28, 2025

(51) Int. Cl.
*A01H 5/00* (2018.01)
*A01H 6/00* (2018.01)

(52) U.S. Cl.
USPC ..... Plt./224
CPC ..... *A01H 6/00* (2018.05)

(58) Field of Classification Search
USPC ..... Plt./224
CPC ..... A01H 5/00
See application file for complete search history.

*Primary Examiner* — Kent L Bell

(57) ABSTRACT

A new and distinct cultivar of *Acer* plant named 'SMNAPK' is disclosed, characterized by finely dissected, lace-like leaves that emerge yellow-green with a reddish-pink tint, maturing green and finally to a red fall color. Vigorous, semi-erect plants that can be grown on their own roots. The new cultivar is an *Acer*, typically produced as an outdoor ornamental plant.

3 Drawing Sheets

Latin name of the genus and species: *Acer palmatum.*
Cultivar denomination: 'SMNAPK'.

BACKGROUND OF THE INVENTION

The new cultivar is a product of a planned breeding program conducted by the inventor to produce *Acer palmatum* plants with new foliage colors and forms as well as plants that can be grown on their own roots (no grafting). The seed parent is *Acer palmatum* 'Autumn Fire', unpatented. The pollen parent is unknown. The open pollination resulting in the new cultivar was made in the summer of 2015 at a nursery in Grand Haven, Michigan. 'SMNAPK' was found and selected as a new cultivar in the summer of 2020 at the same location in Grand Haven, Michigan.

Asexual reproduction of the new cultivar 'SMNAPK' was first performed during summer 2020 in Grand Haven, Michigan by softwood cuttings. Subsequent asexual propagation has shown that the unique features of this cultivar are stable and have been reproduced true to type for five successive generations.

SUMMARY OF THE INVENTION

The cultivar 'SMNAPK' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNAPK'. These characteristics in combination distinguish 'SMNAPK' as a new and distinct *Acer palmatum* cultivar:

1. Finely dissected, lace-like leaves.
2. Young leaves that emerge yellow-green with a reddish-pink tint.
3. Red fall color.

4. Spreading, semi-erect habit.
5. Vigorous growth.
6. Capable of being grown on its own root, grafting not required.

PARENT COMPARISON

Plants of the new cultivar 'SMNAPK' are similar to plants of the seed parent in most horticultural characteristics, however, plants of the new cultivar 'SMNAPK' differ in the following;

1. Sinus depth on leaflet serrations/dissections of the new cultivar is greater than the sinus depth on leaflet serrations/dissections of the seed parent.
2. Plants of the new cultivar are able to be grown on their own roots than plants of the seed parent.

COMMERCIAL COMPARISON

Plants of the new cultivar 'SMNAPK' are similar to plants of *Acer palmatum* 'Emerald Lace', unpatented, in most horticultural characteristics, however, plants of the new cultivar 'SMNAPK' differ in the following;

1. Leaves of the new cultivar are larger than leaves of this comparator.
2. Leaflets of the new cultivar have incisions and appear lace-like, but are not as fine and lacey as this comparator.
3. Newly developed leaves of the new cultivar have more of a reddish-pink coloration/tint than newly developed leaves of this comparator.
4. Plants of the new cultivar are more vigorous than plants of this comparator.

BRIEF DESCRIPTION OF THE PHOTOGRAPHS

The accompanying photograph in FIG. 1 is a mature tree of approximately 6 years, grown outdoors and photographed in late Spring.

Figure 1:
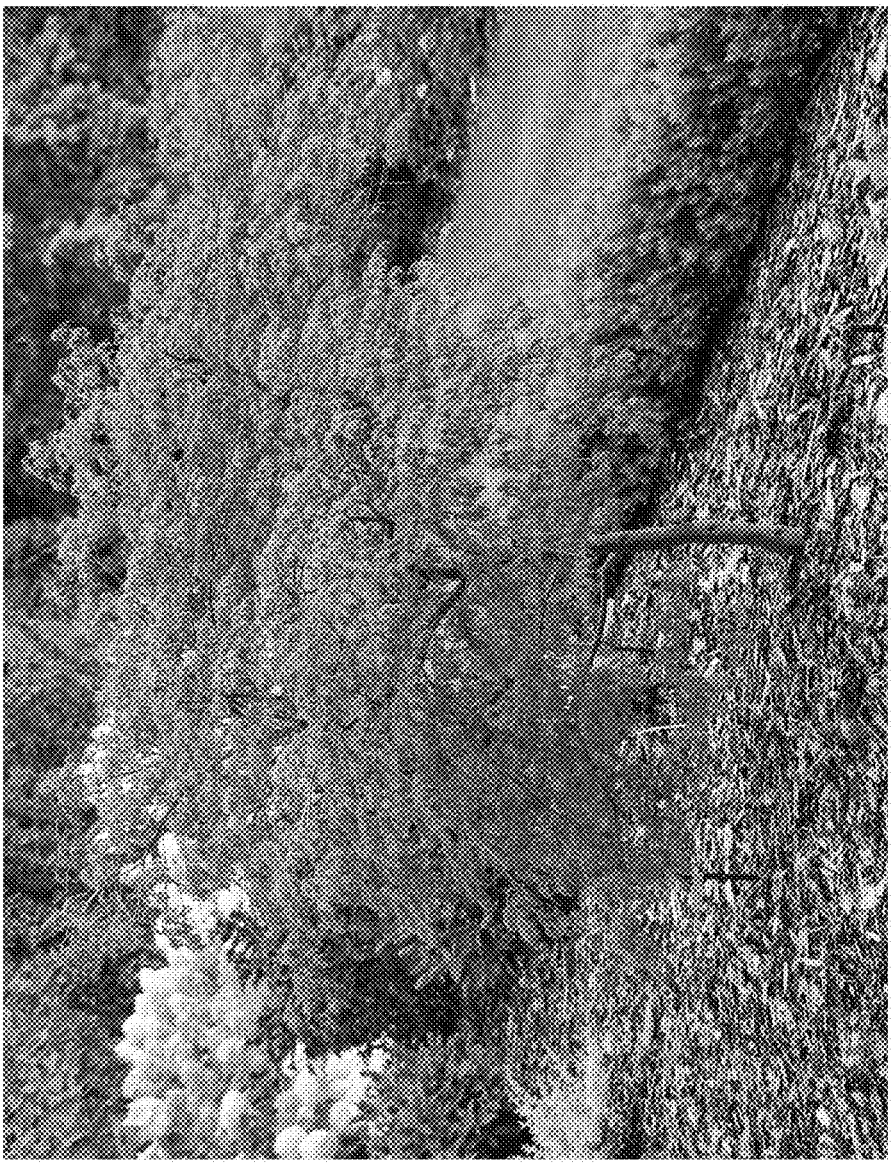
Figure 2:
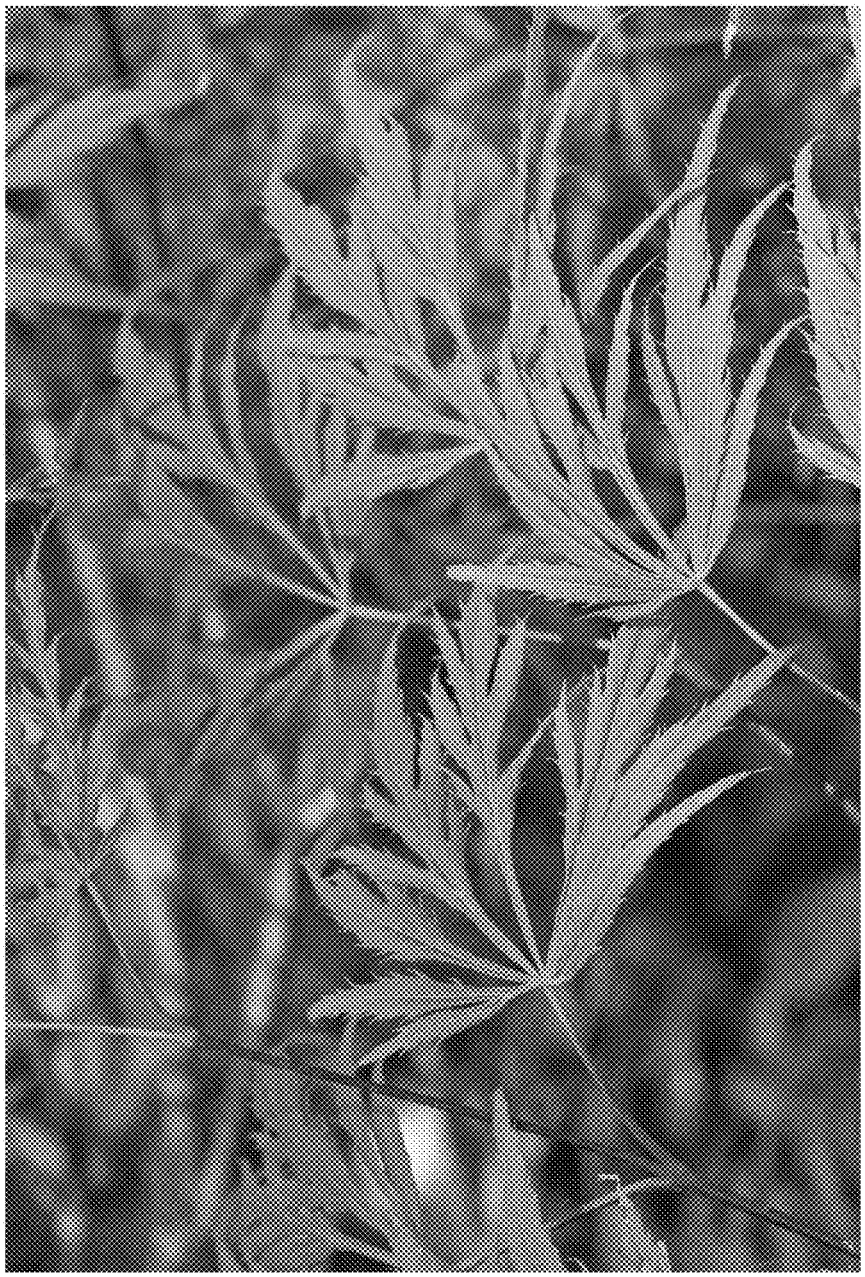
FIG. 2 illustrates in full color a close-up view of typical mature foliage of 'SMNAPK'.
Figure 3:
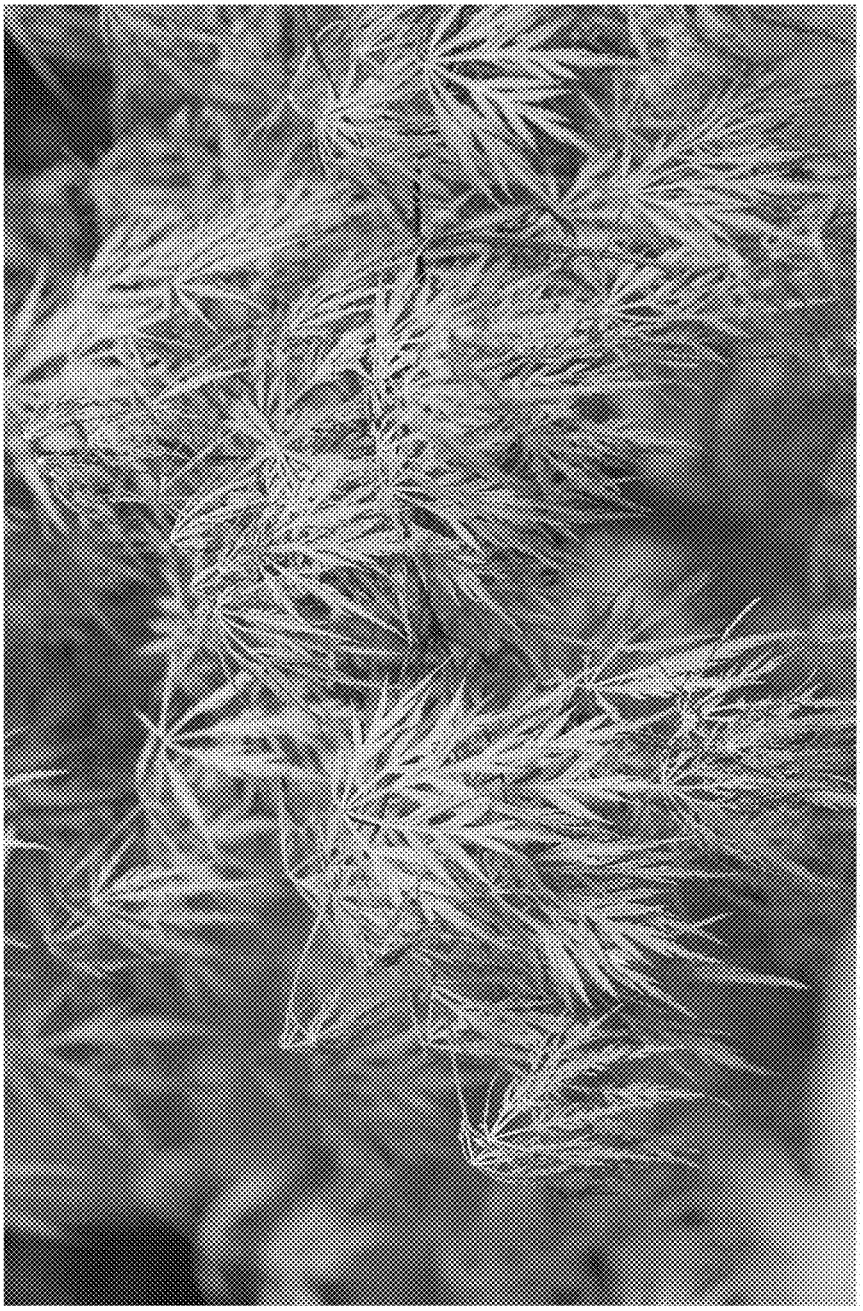
FIG. 3 is typical young foliage with its characteristic reddish-pink tint.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SMNAPK' plants grown in a poly-greenhouse in Grand Haven, Michigan. Plants are approximately 6 to 8 years old, in a 10 gallon nursery container. Temperatures ranged from 5° C. to 10° C. at night to 18° C. to 27° C. during the day. Measurements and numerical values represent averages of typical plant types.

Botanical classification: *Acer palmatum* 'SMNAPK'.

PROPAGATION

Time to initiate roots: About 50 days at approximately 25° C.

Root description: Fibrous, moderately dense, freely branching, thick to thin. brown in color, not accurately measured with an R.H.S. chart.

PLANT

Growth habit: Semi-erect.
Pot size of described plant: 10 gallon.
Growth rate: Moderate.
Height of tree described: 120 cm.
Plant spread of tree described: 175 cm.
Typical mature height: 3 to 4.5 m.
Typical mature spread: 3 to 3.65 m.
Overall plant shape: Round.
Trunk:
- *Trunk color*.—RHS Grey-Brown 199D.
- *Trunk diameter*.—3 cm at 6 years of age.
- *Trunk texture*.—Coarsely textured; non-exfoliating.

Branching characteristics:
- *Quantity of lateral branches*.—Approximately 8-10.
- *Diameter of lateral branches*.—Approximately 2 cm.
- *Length of lateral branches*.—70 to 100 cm.
- *Texture of lateral branches*.—Coarsely textured; non-exfoliating.
- *Color of lateral branches*.—RHS Grey-Brown 199D.
- *Aspect and angle*.—Straight, occurring at a perpendicular angle from the trunk then curving slightly downward.
- *Strength of lateral branches*.—High.
- *Branches occur how far apart*.—Approximately 10 cm.

FOLIAGE

Leaf:
- *Arrangement*.—Opposite.
- *Average length*.—Approximately 4.5 cm.
- *Average width*.—Approximately 6 cm.
- *Shape of blade*.—Palmate.
- *Lobe depth*.—Average 6.0 cm.
- *Number of lobes*.—7 to 9.
- *Apex*.—Acute.
- *Base*.—Truncate.
- *Margin*.—Incised.
- *Texture of top surface*.—Glabrous.
- *Texture of lower surface*.—Glabrous.
- *Leaf internode length*.—4 cm.
- *Color*.—Young foliage upper side: RHS Yellow-Green 144B flushed N144A with a Greyed-Orange 176B and Red 47A tint at the margins, particularly at the apices. Young foliage under side: RHS Yellow-Green 144B flushed N144A with a Greyed-Orange 176B and Red 47A tint at the margins, particularly at the apices. Mature foliage upper side: RHS Green 138A with a very fine Greyed-Orange 176A tint at the margins, particularly at the apices. Mature foliage under side: RHS Green 138B with a very fine Greyed-Orange 176B tint at the margins, particularly at the apices. Fall foliage upper side: Between RHS Greyed-Red 180A and 182A. Fall foliage under side: Between RHS Greyed-Red 182A to 182B.
- *Venation*.—Type: Palmate. Color: Venation color upper side: RHS Green 138A. Venation color under side: RHS Green 138A.
- *Petiole*.—Length: Average 2 cm. Diameter: Average 1 mm. Color: Upper side: RHS Greyed-Orange 166A. Under side: RHS Greyed-Orange 166A. Texture: Glabrous.

FLOWER

Bloom Period: April.
Inflorescence:
- *Arrangement*.—At the terminal ends of lateral branches.
- *Type*.—Compound corymb.
- *Height*.—Approximately 5 cm.
- *Width*.—Approximately 3.5 cm.
- *Quantity of flowers per inflorescence*.—Approximately 20.

Bud:
- *Bud shape*.—Globose.
- *Bud length*.—Approximately 2 mm.
- *Bud diameter*.—Approximately 2 mm.
- *Bud color*.—RHS Greyed-Purple 183A.
- *Base/calyx color*.—RHS Greyed-Purple 183A.

Flower:
- *Average quantity of flowers per lateral branch*.—Approximately 100 inflorescences per lateral branch, equaling approximately 2,000 individual flowers.
- *Diameter*.—Approximately 5 mm.
- *Depth*.—Approximately 3 mm.
- *Shape*.—Whorl, single.
- *Persistent or self-cleaning*.—Self-cleaning.
- *Fragrance*.—None.

Petals:
- *Length*.—Approximately 1.5 mm.
- *Width*.—Approximately 1 mm.
- *Apex*.—Acute.
- *Base*.—Truncate.
- *Shape*.—Elliptic.
- *Margin*.—Entire.
- *Arrangement*.—Whorl, single.
- *Number*.—5.

*Texture*.—Glabrous.

*Color*.—Upper surface at first opening: RHS Green-White 157A with Greyed-Purple 183A at the apex. Upper surface at maturity: RHS Green-White 157A with Greyed-Purple 183A at the apex. Under surface at first opening: RHS Green-White 157A with Greyed Purple 183A at the apex. Under surface at maturity: RHS Green-White 157A with Greyed-Purple 183A at the apex.

Sepals:

*Number*.—5.

*Texture*.—Glabrous

*Arrangement*.—Whorl, single.

*Length*.—Approximately 2 mm.

*Width*.—Approximately 1 mm.

*Shape*.—Oblong.

*Base*.—Truncate.

*Apex*.—Acute.

*Margin*.—Entire.

*Color*.—RHS Greyed-Purple 183A.

REPRODUCTIVE ORGANS

Pistil:

*Number of pistils per flower*.—1.

*Pistil length*.—Approximately 1 mm.

*Stigma shape*.—Filamentous; thread-like.

*Stigma color*.—RHS Greyed-Purple 183A.

*Style color*.—RHS Greyed-Purple 183A.

*Style length*.—Approximately 0.5 mm.

*Ovary color*.—RHS Yellow-Green 144C.

Stamens:

*Stamens quantity*.—8.

*Anther shape*.—Oblong.

*Anther size*.—1 mm.

*Anther color*.—RHS Greyed-Purple 183A.

*Pollen color*.—RHS Yellow 10B.

*Pollen quantity*.—Moderate.

OTHER CHARACTERISTICS

Fruit/seed production: Fruits (samaras) and seeds have yet to be observed.

Disease/pest resistance: Neither resistance nor susceptibility to normal diseases and pests of *Acer* has been observed.

Drought resistance: Moderate.

Temperature tolerance: Low temperature tolerance to approximately 20° F. (−28.9° C.). Tolerates high temperature to at least 95° F. (35° C.). Higher temperatures can be endured if provided with adequate shade.

What is claimed is:

1. A new and distinct cultivar of *Acer* plant named 'SMNAPK' as herein illustrated and described.

* * * * *